United States Patent [19]

Clum et al.

[11] 4,423,041

[45] Dec. 27, 1983

[54] DETACKIFYING COMPOSITIONS

[75] Inventors: Charles E. Clum, Kingston, N.J.; Lanny G. Felty, Pine Grove, Pa.

[73] Assignee: Johnson & Johnson Products, Inc., New Brunswick, N.J.

[21] Appl. No.: 278,283

[22] Filed: Jun. 29, 1981

Related U.S. Application Data

[63] Continuation-in-part of Ser. No. 51,592, Jun. 25, 1979, abandoned.

[51] Int. Cl.$^3$ .................. A61K 31/695; A61K 47/00
[52] U.S. Cl. .................................. 424/184; 252/312; 424/68; 424/358
[58] Field of Search .................. 424/358, 184, 68; 252/312

[56] References Cited

U.S. PATENT DOCUMENTS

| | | | |
|---|---|---|---|
| 2,929,829 | 3/1960 | Morehouse | 424/184 X |
| 2,955,983 | 10/1960 | Messina | 424/68 |
| 3,018,223 | 1/1962 | Siegal | 424/68 |
| 3,198,708 | 8/1965 | Henkin | 424/68 |
| 3,641,239 | 2/1972 | Mohilok | 424/184 |
| 3,953,591 | 4/1976 | Snyder | 424/184 |
| 3,975,294 | 8/1976 | Dumoulin | 424/184 |
| 4,164,563 | 8/1979 | Chang | 424/83 |

FOREIGN PATENT DOCUMENTS

| | | | |
|---|---|---|---|
| 2615654 | 10/1977 | Fed. Rep. of Germany | 424/184 |
| 2642032 | 3/1978 | Fed. Rep. of Germany | 424/184 |
| 2033191 | 12/1970 | France | 424/184 |
| 38-19941 | 6/1963 | Japan | 424/184 |
| 46-14353 | 4/1971 | Japan | 424/358 |
| 187896 | 7/1959 | Sweden | 424/184 |
| 802467 | 10/1958 | United Kingdom | 424/184 |
| 803289 | 10/1958 | United Kingdom | 424/184 |
| 875780 | 8/1961 | United Kingdom | 424/184 |

OTHER PUBLICATIONS

J. A. Ph. Assoc., 12/1957, No. 12, Vol. XLVI, pp. 705-719.
Arneimittel Forschung, 1951, Vol. I, pp. 167-169.
The Military Surgeon, 5/1950, pp. 379-387.
The Journal of Cos. Chemists, 5/1956, vol. 7, No. 3, pp. 234 to 248.

*Primary Examiner*—Dale R. Ore
*Attorney, Agent, or Firm*—Steven P. Berman

[57] ABSTRACT

A detackifying composition for use in emulsion-type personal care compositions comprising a mixture of a silicone fluid and a silicone wax in a ratio of from about 9:1 to 1:3.

5 Claims, No Drawings

4,423,041

DETACKIFYING COMPOSITIONS

This application is a continuation-in-part of Ser. No. 51,592, filed June 25, 1979, now abandoned.

FIELD OF THE INVENTION

This invention relates to compositions comprising combinations of detackifying agents. More specifically, this invention relates to detackifying compositions comprising a mixture of a silicone fluid and a silicone wax in a specific ratio for use in emulsion-type personal care products such as hand lotions, roll-on and cream deodorants and antiperspirants and the like.

BACKGROUND OF THE INVENTION

The treatment of and use on human skin of various products and formulations have been undertaken for countless years. Various formulations have been used on human skin to attempt to keep the skin in a smooth and supple condition or to treat or prevent some condition or unpleasant characteristic. Many of the formulations utilized for such purposes are in the form of an emulsion, and in preparing aesthetically acceptable emulsion products, one must almost always utilize inherently tacky ingredients. Many so-called detackifying agents have been suggested to overcome the undesirable tacky effects of formulations containing such ingredients but generally without much success. An important additional consideration is that any detackifying agent to be utilized in personal care products must be acceptable for human topical application and compatible with the ingredients normally used in such formulations.

SUMMARY OF THE INVENTION

It is an object of this invention to provide improved detackifying compositions.

It is another object of this invention to provide improved detackifying compositions for use in emulsion-type personal care products.

It is a further object of this invention to provide improved detackifying compositions comprising specific combinations of silicone fluids and silicone waxes.

Other objects of this invention will be set forth in or be apparent from the following detailed description of the invention.

The foregoing objects and other features and advantages of the present invention are achieved by compositions comprising specific combinations of detackifying agents. More specifically, these objects are achieved by specific combinations of silicone fluids and silicone waxes which exhibit desirable detackifying effects when utilized in emulsion-type personal care products.

The term "silicone fluid" as used herein refers to a silicone polymer which is fluid at body temperature and which is insoluble in water and cosmetic oils.

The term "silicone wax" as used herein refers to a silicone polymer which is solid or semisolid at body temperature and which is insoluble in water and insoluble or only slightly soluble in cosmetic oils.

DETAILED DESCRIPTION OF THE INVENTION

The detackifying compositions of the present invention comprise a mixture of a silicone fluid and a silicone wax in a ratio of from about 9:1 to 1:3, with a preferred ratio of about 1:1.

The silicone fluids which are useful in the present invention include dimethicone, methicone and cyclomethicone. Dimethicone can be more fully described as polydimethyl siloxane having a molecular weight of from about 500 to about 26,000. Methicone can be more fully described as polymethyl hydrogen siloxane having a molecular weight of from about 500 to about 23,000. Cyclomethicone can be more fully described as the cyclic tetramer of dimethyl siloxane having a moleculor weight of about 296 or the cyclic pentamer of dimethyl siloxane having a molecular weight of about 370. These silicone fluids are readily available from such manufacturers as Dow Corning, General Electric, SWS and Union Carbide under various tradenames, for example, 200 Fluids, SF 96 Fluids, and SWS 101 Fluids, and are suitable for human topical application.

The silicone waxes which are useful in the present invention include stearoxy dimethicone and dimethicone copolyol. Stearoxy dimethicone can be more fully described as a stearoxy dimethyl silane having a molecular weight of about 343 or a distearoxy dimethyl silane having a molecular weight of about 586. Dimethicone copolyol can be more fully described as a dipolyoxyethylene dimethyl silane having a molecular weight of from about 1600 to about 2000. These silicone waxes are readily available from such manufacturers as Dow Corning and SWS under various tradenames such as QF Waxes and F Copolomers and are suitable for human topical application. As discussed above, the detackifying agents should be utilized in a ratio of silicone fluid to silicone wax of from about 9:1 to 1:3, preferably about 1:1. If mixtures of the detackifying agents are utilized outside these ratios, there may be a significant loss of the desired detackifying properties. It would appear that one should utilize about one or more parts of the detackifying compositions of the present invention to each of five parts of tacky components present in the various products. Thus, it is noted that the amount of the detackifying compositions utilized depends on the amount of tacky components present in the various emulsion-type personal care products and the actual percentage of the detackifying compositions utilized would vary with each formulation.

The detackifying compositions of this invention are useful in emulsion-type personal care products such as hand lotions, roll-on and cream deodorants and antiperspirants, moisturizers, facial emollients, body creams, make-up preparations and the like. Although applicants do not wish to be bound by the following statement, it is speculated that the detackifying compositions of the present invention work successfully whereas the same detackifying agents alone are not successful because in an emulsion system the system goes from a mixture of oil and water to a film of oil when the water evaporates and detackification is needed at both stages. It appears that when silicone fluid detackifying agents alone are utilized, they are only useful in the emulsion stage and are not effective when the water evaporates from the emulsion system; and when silicone wax detackifying agents alone are utilized, these agents are only effective after the water has evaporated leaving a film of oil. It is, therefore, suggested that the compositions of the present invention are effective at each of the stages of the emulsion system thereby providing a total detackifying effect to the emulsion-type personal care product.

Specific embodiments of the present invention are illustrated by the following examples. It will be understood, however, that the invention is not confined to the specific limitations set forth in the individual examples, but rather to the scope of the appended claims.

EXAMPLE 1

A hand lotion is prepared in a mixing vessel by first dispersing 40 grams of propylene glycol in 813.25 grams of water and thereafter dispersing 3 grams of a stabilizer, Carbomer 934, and heating the resultant mixture to 80° C. In a separate vessel is charged 10 grams of dimethicone; 10 grams stearoxy dimethicone; 30 grams dimer acid; 25 grams myristyl myristate; 15 grams isopropyl palmitate; 12.5 grams of an emulsifier, Polysorbate-61; 10 grams cetyl alcohol; 10 grams stearyl alcohol; 7.5 grams sorbitan stearate; 3 grams benzyl alcohol; 2 grams propylparaben; 3 grams methylparaben; and the components are mixed and then added to the first vessel with mixing. 3.25 grams of sodium hydroxide are then added and the mixture is cooled to 50° C. and then 2.5 grams of fragrance are added. The resulting mixture is cooled to 30° C. and consists of the following ingredients:

| Ingredients | % w/w |
|---|---|
| dimethicone | 1.000 |
| stearoxy dimethicone | 1.000 |
| dimer acid | 3.000 |
| distilled water | 81.325 |
| propylene glycol | 4.000 |
| myristyl myristate | 2.500 |
| isopropyl palmitate | 1.500 |
| Polysorbate-61 | 1.250 |
| cetyl alcohol | 1.000 |
| stearyl alcohol | 1.000 |
| sorbitan stearate | 0.750 |
| sodium hydroxide | 0.325 |
| Carbomer 934 | 0.300 |
| benzyl alcohol | 0.300 |
| methyl paraben | 0.300 |
| fragrance | 0.250 |
| propyl paraben | 0.200 |
| | 100.00 |

EXAMPLE II

A substantially similar hand lotion to the hand lotion in EXAMPLE I is prepared in the same manner and consists of the following ingredients:

| Ingredients | % w/w |
|---|---|
| mineral oil | 6.000 |
| dimer acid | 4.000 |
| propylene glycol | 4.000 |
| myristyl alcohol | 3.000 |
| isopropyl palmitate | 2.000 |
| petrolatum | 2.000 |
| myristyl myristate | 1.000 |
| Polysorbate-61 | 1.000 |
| stearic acid | 1.000 |
| sorbitan stearate | 0.800 |
| sodium hydroxide | 0.317 |
| benzyl alcohol | 0.300 |
| methyl paraben | 0.300 |
| Carbomer 934 | 0.250 |
| fragrance | 0.250 |
| propyl paraben | 0.200 |
| distilled water | q.s. to 100% |

As can be readily noted, the detackifying mixture of the present invention utilized in the hand lotion formulation of EXAMPLE I has been deleted from the hand lotion formulation of EXAMPLE II and has been replaced by mineral oil which is taught in the art to be useful as a detackifying agent.

The detackification properties of the compositions of the present invention are evaluated by the following test procedures. In the first procedure, a haptic or skin feel test is conducted by a panel of experienced evaluators in the following manner. Each individual washes his hands with soap and water and thoroughly dries the hands and then a constant quantity of the hand lotion is applied. The lotion is then spread onto and rubbed into the skin in a uniform motion until the aqueous portion of the lotion has evaporated and the lotion subjectively to the evaluator appears to vanish from the surface of the skin. The rub-in time of the lotion from the start of spreading to the point of vanish is noted as are various skin feel properties, i.e., tackiness, greasiness, oiliness and the like. These properties are compared to an arbitrary standard thus permitting the evaluation and ranking of various lotions on a scale of 1 to 5 for various properties with a rating of 1 being considered the best.

A second test procedure involves the utilization of a panel of consumers who are given two containers of a product, e.g., hand lotion, and are asked to utilize each container for a period of one week. They are then given a questionnaire to be filled out and returned which covers specific likes and dislikes regarding each product as well as specific attributes of each product, e.g., tackiness, if the product is a hand lotion.

When the compositions of EXAMPLES I and II were subjected to each of the above test procedures, a clear preference with respect to the lack of tackiness was perceived by both the experienced evaluators and the consumers toward the hand lotion composition of EXAMPLE I as compared with the hand lotion composition of EXAMPLE II.

EXAMPLE III

A hand lotion composition is prepared according to the procedure of EXAMPLE I and consists of the following ingredients:

| Ingredients | % w/w |
|---|---|
| dimethicone | 1.000 |
| stearoxy dimethicone | 1.000 |
| dimer acid | 3.000 |
| propylene glycol | 4.000 |
| myristal myristate | 2.500 |
| isopropyl palmitate | 1.500 |
| Polysorbate-61 | 1.250 |
| cetyl alcohol | 1.000 |
| stearyl alcohol | 1.000 |
| sorbitan stearate | 0.800 |
| sodium hydroxide | 0.325 |
| benzyl alcohol | 0.300 |
| Carbomer 934 | 0.300 |
| methyl paraben | 0.300 |
| fragrance | 0.250 |
| propyl paraben | 0.200 |
| distilled water | q.s. to 100% |

The hand lotion of EXAMPLE III was tested against a leading commercially available hand lotion product in accordance with the test procedures set forth in EXAMPLE II and a preference in terms of lack of tackiness was indicated for the composition of EXAMPLE III in each of the two test procedures.

EXAMPLE IV

A roll-on antiperspirant composition is prepared in a mixing vessel as follows: 12.5 grams of a magnesium aluminum silicate thickener is dispersed in 237.5 grams of water at a temperature of 70° C. In a separate vessel is charged 25 grams of a mineral oil and lanolin alcohol mixture, Amerchol L101; 10 grams of a lanolin derivative, laneth 10 acetate; 5 grams of cetyl alcohol; 10 grams glycerine; 20 grams of a polyethylene glycol 40 stearate emulsifier; 25 grams of dimethicone and 10 grams of stearoxy dimethicone which is heated to 60° C. with agitation and combined in the mixing vessel with the water. The total mixture is cooled to 32° C. A slurry consisting of 110 grams of 50% aluminum chlorhydrate solution and 30 grams of aluminum hydroxide is added with mixing followed by 5 grams of fragrance. The resulting composition consists of the following ingredients:

| Ingredients | % w/w |
| --- | --- |
| dimethicone | 5.00 |
| stearoxy dimethicone | 2.00 |
| aluminum chlorhydrate | 20.00 |
| aluminum hydroxide | 10.00 |
| distilled water | 50.00 |
| Amerchol L101 | 4.00 |
| polyethylene glycol-40 stearate | 3.00 |
| laneth-10-acetate | 2.00 |
| glycerine | 2.00 |
| magnesium aliminum silicate | 1.50 |
| fragrance | 0.50 |
| | 100.00 |

EXAMPLE V-VII

Three additional roll-on antiperspirant compositions are prepared in accordance with the procedure of EXAMPLE IV and consist of the following ingredients:

| | EXAMPLES | | |
| --- | --- | --- | --- |
| Ingredients | V % w/w | VI % w/w | VII % w/w |
| dimethicone | — | 5.00 | — |
| stearoxy dimethicone | 2.00 | — | — |
| aluminum chlorhydrate | 20.00 | 20.00 | 20.00 |
| aluminum hydroxide | 10.00 | 10.00 | 10.00 |
| distilled water | 55.00 | 52.00 | 57.00 |
| Amerchol L101 | 4.00 | 4.00 | 4.00 |
| polyethylene glycol-40 stearate | 3.00 | 3.00 | 3.00 |
| laneth-10-acetate | 2.00 | 2.00 | 2.00 |
| glycerine | 2.00 | 2.00 | 2.00 |
| magnesium aluminum silicate | 1.50 | 1.50 | 1.50 |
| fragrance | .50 | .50 | .50 |

The detackifying properties of the compositions of the present invention when utilized in deodorants or antiperspirant compositions can be evaluated by the following test procedure. A panel of experienced evaluators place samples of the products on the back of the hand and rub into the skin until dry and then observe the tackiness or lack thereof. The evaluators also utilize the product under the arm in the normal manner to observe the tackiness and rank the products compared to an arbitrary standard.

When the compositions of EXAMPLES IV-VII were tested in the above manner, the composition of EXAMPLE IV containing the detackifier composition of the present invention was significantly preferred over the compositions of EXAMPLES V, VI and VII.

EXAMPLE VIII

A hand lotion composition is prepared according to the procedure of EXAMPLE I and consists of the following ingredients:

| | % w/w |
| --- | --- |
| dimer acid | 3.00 |
| isopropyl palmitate | 1.50 |
| Polysorbate 61 | 1.25 |
| myristyl myristate | 2.50 |
| stearoxy dimethicone | 0.20 |
| dimethicone | 1.80 |
| cetyl alcohol | 1.00 |
| stearyl alcohol | 1.00 |
| sorbitan stearate | 0.75 |
| glycerol stearate | 1.50 |
| glycerol dilaurate | 0.50 |
| benzyl alcohol | 0.30 |
| Carbopol 934 | 0.30 |
| propylene glycol | 4.00 |
| methyl paraben | 0.30 |
| propyl paraben | 0.20 |
| NaOH soln (10%) | 3.25 |
| fragrance | 0.20 |
| distilled water | 76.45 |

EXAMPLE IX

A hand lotion composition is prepared according to the procedure of EXAMPLE I and consists of the following ingredients:

| | % w/w |
| --- | --- |
| dimer acid | 3.00 |
| isopropyl palmitate | 1.50 |
| Polysorbate 61 | 1.25 |
| myristyl myristate | 2.50 |
| stearoxy dimethicone | 0.50 |
| dimethicone | 1.50 |
| cetyl alcohol | 1.00 |
| stearyl alcohol | 1.00 |
| sorbitan stearate | 0.75 |
| glycerol stearate | 1.50 |
| glycerol dilaurate | 0.50 |
| benzyl alcohol | 0.30 |
| Carbopol 934 | 0.30 |
| propylene glycol | 4.00 |
| methyl paraben | 0.30 |
| propyl paroben | 0.20 |
| NaOH soln (10%) | 3.25 |
| fragrance | 0.20 |
| distilled water | 76.45 |

EXAMPLE X

A hand lotion composition is prepared according to the procedure of EXAMPLE I and consists of the following ingredients:

| | % w/w |
| --- | --- |
| dimer acid | 3.00 |
| isopropyl palmitate | 1.50 |
| Polysorbate 61 | 1.25 |
| myristyl myristate | 2.50 |
| stearoxy dimethicone | 1.50 |
| dimethicone | 0.50 |
| cetyl alcohol | 1.00 |
| stearyl alcohol | 1.00 |
| sorbitan stearate | 0.75 |
| glycerol stearate | 1.50 |
| glycerol dilaurate | 0.50 |
| benzyl alcohol | 0.30 |
| Carbopol 934 | 0.30 |

| | % w/w |
|---|---|
| propylene glycol | 4.00 |
| methyl paraben | 0.30 |
| propyl paraben | 0.20 |
| NaOH soln (10%) | 3.25 |
| fragrance | 0.20 |
| distilled water | 76.45 |

EXAMPLE XI

A hand lotion composition is prepared according to the procedure of EXAMPLE I and consists of the following ingredients:

| | % w/w |
|---|---|
| dimer acid | 3.00 |
| isopropyl palmitate | 1.50 |
| Polysorbate 61 | 1.25 |
| myristyl myristate | 2.50 |
| dimethicone copolyol | 1.00 |
| dimethicone | 1.00 |
| cetyl alcohol | 1.00 |
| stearyl alcohol | 1.00 |
| sorbitan stearate | 0.75 |
| glycerol stearate | 1.50 |
| glycerol dilaurate | 0.50 |

| | % w/w |
|---|---|
| benzyl alcohol | 0.30 |
| Carbopol 934 | 0.30 |
| propylene glycol | 4.00 |
| methyl paraben | 0.30 |
| propyl paraben | 0.20 |
| NaOH soln (10%) | 3.25 |
| fragrance | 0.25 |
| distilled water | 76.40 |

I claim:
1. A detackifying composition consisting essentially of a mixture of a silicone fluid and a silicone wax in a ratio of 9:1 to 1:3 wherein said silicone fluid is selected from the group consisting of dimethicone, methicone and cyclomethicone and said silicone wax is selected from the group consisting of stearoxy dimethicone and dipolyoxyethylene dimethyl silane.
2. A detackifying composition according to claim 1 wherein the silicone fluid is dimethicone.
3. A detackifying composition according to claim 1 wherein the silicone wax is stearoxy dimethicone.
4. A detackifying composition according to claim 1 wherein the silicone fluid is dimethicone and the silicone wax is stearoxy dimethicone.
5. A detackifying composition according to claim 1 wherein the ratio of silicone fluid to silicone was is about 1:1.

* * * * *